United States Patent [19]
Lightner

[11] Patent Number: 6,133,328
[45] Date of Patent: Oct. 17, 2000

[54] PRODUCTION OF SYNGAS FROM A BIOMASS

[76] Inventor: Gene E. Lightner, 706 SW. 296th St., Federal Way, Wash. 98023-3549

[21] Appl. No.: 09/510,264

[22] Filed: Feb. 22, 2000

[51] Int. Cl.[7] .............................. C07C 27/00; C07C 1/00; C10J 3/00
[52] U.S. Cl. ......................... 518/700; 518/702; 518/703; 518/704; 252/373; 48/209
[58] Field of Search .................................. 518/702, 703, 518/704, 700; 252/373; 48/209

[56] References Cited

U.S. PATENT DOCUMENTS

| | | | |
|---|---|---|---|
| 4,498,909 | 2/1985 | Milner et al. ............................. | 48/209 |
| 5,637,259 | 6/1997 | Galuszka et al. ....................... | 252/373 |

OTHER PUBLICATIONS

Chem. Eng HndBk. Ed–Perry 3rd. Ed. pp: 1579–1580, 1950.
*Process Heat Transfer*, D.Q. Kern, pp: 668–670, 1950.
Internet: Mar. 15, 2000 Univ. of Hawaii "Biomass Gasification".
Internet: Mar. 15, 2000 Nat'l Res. Energy Labs "Bioethanol Technology".

*Primary Examiner*—Johann Richter
*Assistant Examiner*—J. Parsa

[57] ABSTRACT

This is a method to furnish synthesis gas obtained from a biomass. A description of a synthesis gas production method is presented by providing a supply of biomass, air and steam to a vessel. A heat exchanger is provided for heating ambient air to provide a supply of heated air to the vessel and a dryer is provided to remove moisture from a biomass to provide a supply of substantially moisture free biomass to the vessel. Subsequently reacting with the substantially moisture free biomass in the vessel with the heated air forms incandescent carbon and a flue gas. A bed of solids for storage of thermal sensible heat from the flue gas is provided. Upon turning off the heated air, a supply of steam, created from water provided to the heated bed of solids, is employed to purge the remaining flue gas and form a blanket of steam above the incandescent carbon. When the carbon is incandescent, and the heated air is turned off, steam is added to the steam blanketed incandescent carbon to create a water gas containing hydrogen and carbon monoxide. The procedure is then repeated. The water gas is modified by reaction with steam to produce additional hydrogen to form an adjusted syngas with a mole ratio of hydrogen to carbon monoxide of about 2. Combustion residue from the biomass is separated from the carbon for disposition or disposal.

21 Claims, 2 Drawing Sheets

PRODUCTION OF SYNGAS FROM A BIOMASS

BACKGROUND OF THE INVENTION

Synthesis gas, termed syngas, is usually derived from non-replaceable fossil fuels. Syngas is often converted to methanol for subsequent use as a chemical, solvent or fuel.

The formation of syngas derived from petroleum materials such as methane is reported in several publications such as U.S. Pat. No. 5,637,259. Additional reporting on petroleum materials employed for formation of syngas is not concerned with biomass and will subsequently not be detailed or additionally reported further.

Throughout the world there is increasing interest in converting renewable biomass to usable products to avoid consumption of non-replaceable fossil fuels. Biomass is associated with non-fossil organic materials that contain fundamental energy derived from the sun. A biomass is often selected from the group consisting of wood, waste paper and municipal solid waste including an individual or a combination of these biomass materials.

Conversion of biomass energy to practical non-stationary fuels is desirable. Present day interest in biomass is to provide an alternative fuel source to avoid dependence on unreliable imported petroleum crude oil for fuels.

Biomass can be used to yield synthesis gas for production of methanol, thus biomass may provide an alternative liquid fuel source.

Manufacture of water gas, as described in Chemical Engineers Handbook third edition, edited by Perry, pages 1579–1580, begins with coal or coke as a source of carbon transported to a steel shell about 3 to about 10 ft. diameter lined with insulation and fire brick. The coal or coke is dependent on oxygen in air for combustion to form incandescent carbon. As soon as the carbon bed obtains satisfactory temperature the air supply is shut off and steam is admitted to produce the desired water gas. The admitted steam rapidly reduces the carbon bed temperature. The steam flow is then discontinued and air flow is admitted to the steel shell to raise the carbon temperature to incandescence thus repeating the sequence. New developments for employment of low cost tonnage oxygen is being investigated for use in continuous water gas manufacture as reported by Perry. A present day continuous process for biomass gasification is being developed at the university of Hawaii and is illustrated and explained by "Biomass Gasification" on the internet. The process employs oxygen and biomass to produce water gas converted by steam to manufacture syngas. The syngas is then transformed from a gas to form liquid methanol. During biomass gasification hydrocarbons and tars form in the syngas. The problem of formation of hydrocarbons and tars is being addressed by researchers, reported by "Synthesis Gas Conditioning from Biomass" on the internet, at the National Research Energy Labs (NREL). Destruction of tars in a fluidized-bed using a recently developed catalyst is reported. "Bioethanol Technology", reported by the internet, researchers at, NREL, syngas from biomass can be fermentated by anaerobic bacteria to convert biogas to form ethanol.

Present day motor vehicles employ internal combustion engines operating with petroleum based liquid fuels. In the future internal combustion engines will be replaced with other power sources such as hydrogen based fuel cells. Fuel cells will convert hydrogen to electricity from oxygen in air to form water vapor which is pollution free. The electricity thus formed will be used to supply power for the motor vehicles. The problem with hydrogen powered vehicles is apparently the lack of renewable energy. Methanol, from syngas, located in a fuel tank in the vehicle can be converted to form hydrogen capable of meeting this need.

It is therefore an object of this invention to obviate many of the limitations or disadvantages of the prior art.

The present concern is about synthesis gas obtained from a biomass.

A distinct object of this invention is to employ air and water to produce synthesis gas from a biomass.

A further object of this invention is to manufacture methanol or liquid fuels from synthesis gas.

Another object of this invention is to avoid use of gasoline powered internal combustion engines.

Still another object of this invention is to produce a substantial reduction in air pollution.

Yet another object of this invention is to provide a liquid containing hydrogen capable of generating electrical power from a fuel cell.

An additional object of this invention is to provide a liquid fuel from renewable energy.

In addition an object of this invention is to furnish a supply of syngas obtained from a biomass.

A further objective of this invention is to provide a method to avoid employment of tonnage oxygen to produce synthesis gas from a biomass. With the above and other objects in view, this invention relates to the novel features and alternatives and combinations presently described in the brief description of the invention.

BRIEF DESCRIPTION OF THE INVENTION

The present invention in its broadest aspect, establishes a method to provide a synthesis gas obtained from a biomass. A supply of biomass, air and steam is advanced to a vessel for combustion of the biomass to form incandescent carbon and a flue gas. A heat exchanger is provided for heating ambient air, from the flue gas, to provide a supply of heated air to the vessel A dryer is provided to remove moisture from a biomass, from the flue gas, to provide a supply of substantially moisture free biomass to the vessel. A bed of solids for storage of thermal sensible heat from the flue gas is provided. Consequently to turning off the heated air, a supply of steam is created from water provided to the heated bed of solids storing thermal sensible heat from the flue gas. Steam is employed to purge the remaining flue gas above the incandescent carbon and form a blanket of steam above the incandescent carbon. When the carbon is incandescent, and the heated air is turned off, steam is added to the steam blanketed incandescent carbon to create a syngas containing hydrogen and carbon monoxide. The procedure is then repeated. Combustion residue from the biomass is separated from the carbon for disposition or disposal.

Characteristics of the invention include;

Ambient air is heated from flue gas to provide heated air to the vessel. Biomass is substantially dried by the flue gas to provide substantially dried biomass to the vessel. Thermal sensible heat from the flue gas is stored in a provided bed of solids. When the heated air to the vessel is turned off, ending the flow of the flue gas, a supply of steam is created from water provided to the heated bed.

A portion of the supply of steam is employed to purge the remaining flue gas above the incandescent carbon.

The remaining supply of steam is transmitted to the incandescent carbon to react with the incandescent carbon and form water gas containing hydrogen and carbon monoxide. The water gas is then reacted with steam to produce additional hydrogen to form a syngas with a mole ratio of about 2.0 of hydrogen to carbon monoxide. Combustion residue from the biomass is separated from the vessel for disposition or disposal.

BRIEF DESCRIPTION OF THE DRAWINGS

The features that are considered characteristic of this invention are set forth in the appended claims. This invention, however, both as to its origination and method of operations as well as additional advantages will best be understood from the following description when read in conjunction with the accompanying drawings in which:

DETAILED DESCRIPTION OF THE PREFERRED EMBODIMENT

In the preferred embodiment of the present invention, a means of providing a syngas derived from a biomass. The syngas containing hydrogen and carbon monoxide is produced from substantially moisture free biomass, heated air and steam supplied for that specific purpose.

Figure 1:
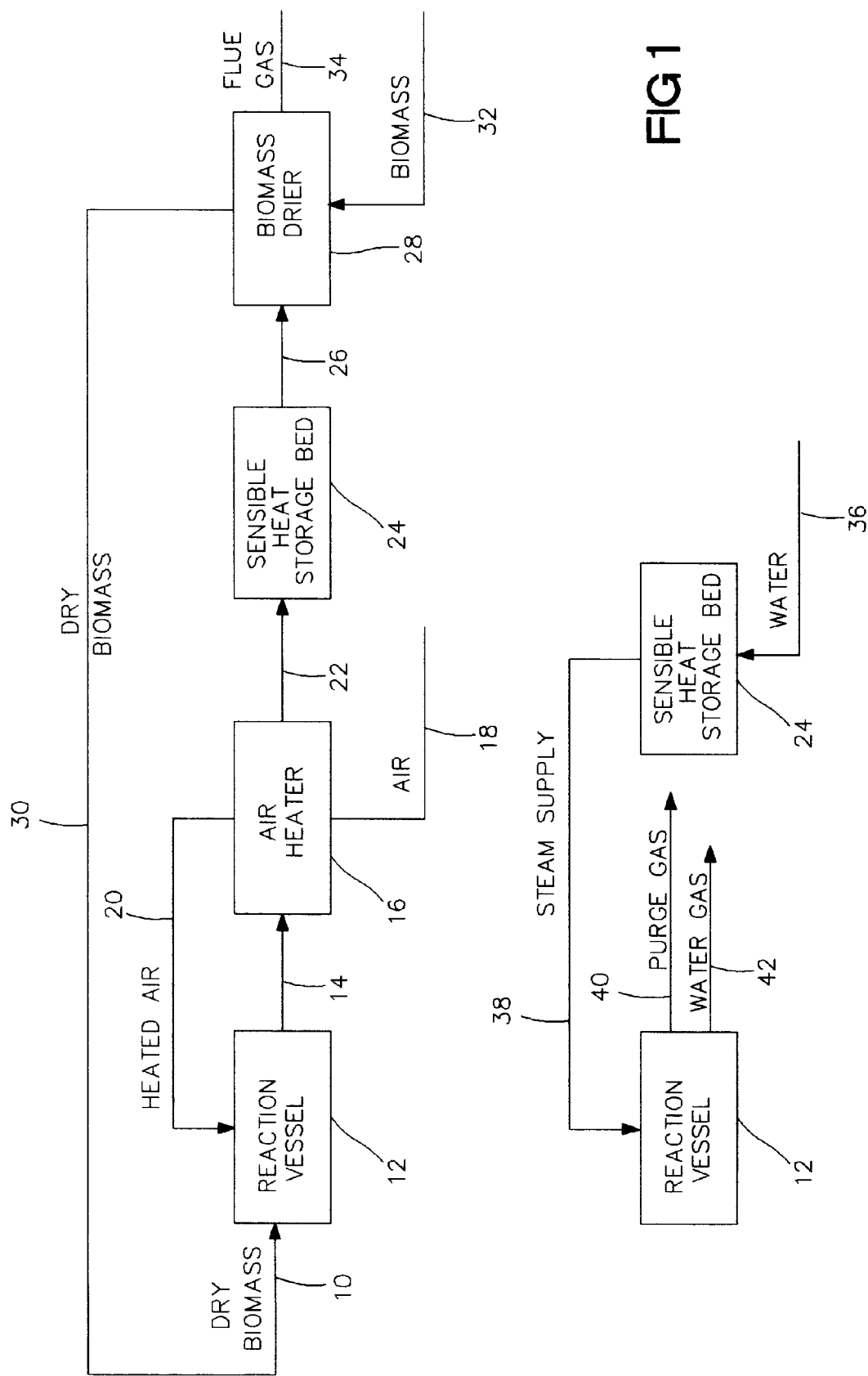
FIG. 1 is a flow sheet denoting the invention as set forth in the appended claims.

The flow diagram of FIG. 1 illustrates the general preferred embodiment of the present invention. In the diagram, rectangles represent stages, operations or functions of the present invention and not necessarily separate components. Arrows indicate direction of flow of material in the method. The method portrayed in FIG. 1 will take place at a range of about 1000° C.

FIG. 1, is divided into two time separated periods which represent a continuation of time.

Referring to FIG. 1, dry biomass 10 is conveyed to a reaction vessel 12, and heated air 20 is conveyed to the reaction vessel 12 to form incandescent carbon and a flue gas 14 which is conducted to an air heater 16 where ambient air 18 is heated to form heated air 20 conveyed to the reaction vessel 12. The flue gas containing sensible heat energy 22 is conveyed to a sensible heat storage bed 24 where sensible heat from the flue gas 22 is stored. Flue gas exiting from the sensible heat storage bed 24 where flue gas is conveyed to a biomass dryer 28 fed by un-dried biomass to provide dry biomass 30 to the reaction vessel 12. The reaction vessel 12 forms incandescent carbon from combustion of dry biomass 10 and heated air 20 When the incandescent carbon has attained steam conversion temperature, the heated air 20 is turned off thus completing the first tine period. With the heated air 20 turned off, water 36 is conveyed to the sensible heat storage bed 24 where water forms a supply of steam 38 which is transported to the reaction vessel 12 to purge flue gas from the vessel and form a purge gas 40. The remaining supply of steam 38 reacts with the incandescent carbon contained in the reaction vessel 12 to supply water gas 42. Thus completing the second tine period to complete the time cycle which is then repeated. The sensible heat storage bed 24 is similar to beds decribed by D. Q. Kern in PROCESS HEAT TRANSFER pages 668–670.

The flue gas containing sensible heat energy 14 is employed in three serial applications; to form heated air 20, the sensible heat storage bed 24 and a biomass dryer 28 for drying biomass 32. Thus sensible heat energy from the flue gas is employed in three operations to reduce the heat energy contained in the flue gas. Incandescent carbon temperature in the vessel 12 is regulated to maintain a temperature of about 1000 degrees Celsius. The incandescent carbon temperature is regulated to increase the temperature by admitted heated air or steam to substantially decrease the incandescent carbon temperature. The water gas 42 is formed in the reaction vessel 12 by admitting steam 38 to form hydrogen and carbon dioxide to produce a water gas 42. The heated air 20 and substantially moisture free biomass 10 are, in essence, admitted to the reaction vessel 12 concurrently. The vessel 12 may be at atmospheric pressure or pressurized above atmospheric pressure. The heated air 20 and steam supply 38 are substantially employed alternately to complete the time cycle. The heated air 20 is heated from flue gas 14 to produce air temperature in excess of ambient temperature.

Figure 2:
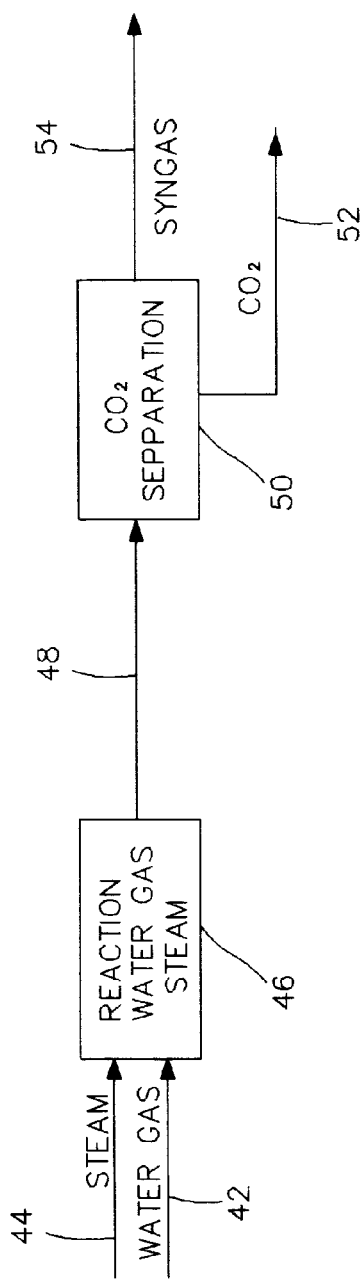
FIG. 2 is a flow sheet denoting a method to react water gas to form syngas and remove formed carbon dioxide from the syngas.

Referring to FIG. 2, steam 44 and water gas 42 are conveyed to a reaction with steam and water 46 to produce a syngas 48 containing hydrogen, carbon monoxide and carbon dioxide which is transported to a stage for carbon dioxide separation 50 to separate carbon dioxide 52 to produce a syngas 54 substantially free of carbon dioxide. The stage for carbon dioxide separation 50 may conceivably contain water to form carbonic acid from the carbon dioxide contained in the syngas. The carbonic acid would be substantially removed from the water by several means. For example, an ion exchange membrane to employed to free the carbonic acid from water and release the carbonic acid as gaseous carbon dioxide. Water gas 42 is concentrated by reaction 46 with steam 44 to form syngas 48 containing an adjusted desired ratio of hydrogen to carbon monoxide of about 2-1 mole ratio. The formed syngas containing hydrocarbons and tars, is often reacted with steam to remove the hydrocarbons and tars and produce additional syngas. The syngas 54 may be pressurized and separated from contained carbon dioxide.

Figure 3:
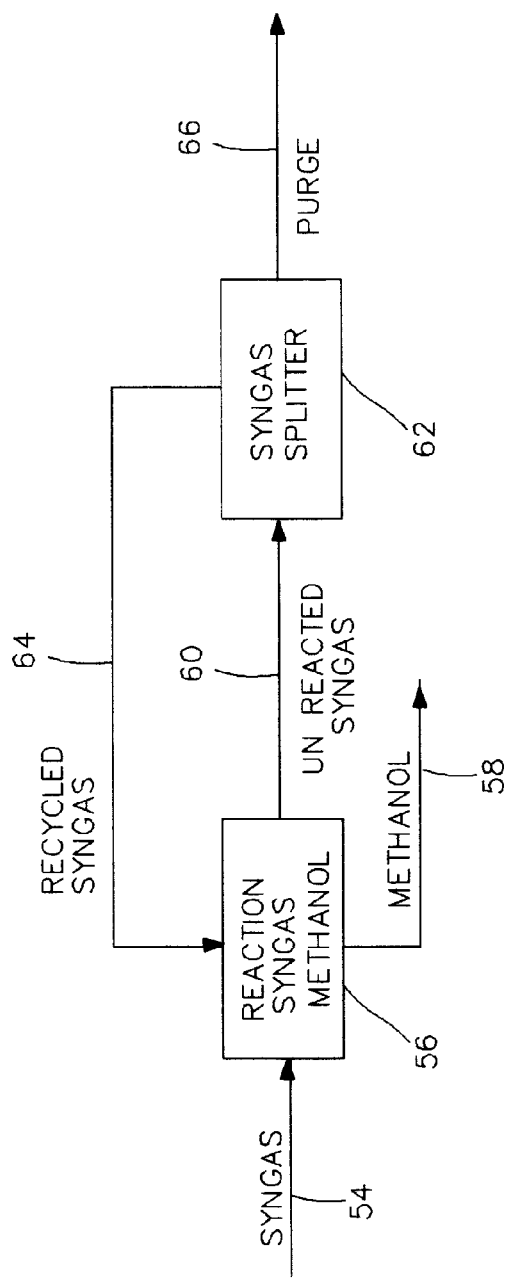
FIG. 3 is a flow sheet denoting a method to react syngas with steam to produce methanol.

Referring to FIG. 3, syngas 54 is transported to a reaction stage 56 where syngas reacts to form methanol and an un-reacted portion of syngas 60 and fed to a syngas splitter 62 a fraction of the syngas is purged 66 and the remaining fraction of syngas is recycled to the syngas reaction stage 56 to form additional methanol. The syngas reaction stage 56 may, and often does, contain a catalyst.

What is claimed is:

1. A method to produce synthesis gas from a biomass, which comprises:

providing a supply of substantially moisture free biomass, and providing a supply of heated air to said vessel; and providing a heat exchanger to heat air to provide a supply of heated air to said vessel; and providing a vessel for reaction of said substantially moisture free biomass; and providing a bed of solids for storage of sensible heat; and providing a supply of water to said bed of solids containing stored sensible heat, and providing a dryer to remove moisture from a biomass, and reacting said substantially moisture free biomass in said vessel with said heated air to form incandescent carbon and a flue gas, and heating ambient air with said heat exchanger supplied from sensible heat in said flue gas to provide said heated air to said vessel, and storing sensible heat from said flue gas to store heat in said bed of solids, and drying a biomass in said dryer with said flue gas to remove moisture from a biomass to produce substantially moisture free biomass, and adding said water to said bed of solids containing stored heat to provide a supply of steam, and providing a supply of steam from said bed of solids to said vessel; and reacting said incandescent carbon with said steam to form a water gas, and reacting said water gas with steam to produce a synthesis gas thereby synthesis gas is produced from a biomass.

2. The method of claim 1 where said substantially moisture free biomass is a biomass selected from the group consisting of wood, waste paper and municipal solid waste or combination thereof.

3. The method of claim 1 where said vessel is pressurized.

4. The method of claim 1 where said synthesis gas is pressurized.

5. The method of claim 1 where said heated air is in excess of ambient temperature.

6. The method of claim 1 where said heated air is heated from said flue gas to produce air temperature in excess of ambient temperature.

7. The method of claim 1 where said incandescent carbon is produced from said substantially moisture free biomass by combustion from air of temperature in excess of ambient temperature.

8. The method of claim 1 where said synthesis gas contains carbon monoxide and hydrogen.

9. The method of claim 1 where said synthesis gas is transformed to methanol.

10. The method of claim 1 where said synthesis gas is transformed to methanol employing a catalyst.

11. The method of claim 1 where said heated air is in excess of atmospheric pressure.

12. The method of claim 1 where said heated air and said steam are substantially employed alternately.

13. The method of claim 1 where said heated air and said substantially moisture free biomass are substantially admitted to said vessel concurrently.

14. The method of claim 1 where said incandescent carbon is of a temperature of about 1000 degrees Celsius.

15. The method of claim 14 where said incandescent carbon temperature is regulated by admitted heated air to substantially increase the incandescent carbon temperature.

16. The method of claim 14 where said incandescent carbon temperature is regulated by admitted steam to substantially decrease the incandescent carbon temperature.

17. The method of claim 1 where in said water gas is reacted with steam to form hydrogen and carbon dioxide to produce a synthesis gas containing a ratio of hydrogen to carbon monoxide of about 2-1 mole ratio.

18. The method of claim 17 where said synthesis gas, containing carbon dioxide is separated from the synthesis gas to produce synthesis gas substantially free of carbon dioxide.

19. The method of claim 1 where said synthesis gas containing hydrocarbons and tars in said synthesis gas is reacted with steam to form hydrogen to produce a synthesis gas substantially free of hydrocarbons and tars.

20. The method of claim 1 where steam is employed to purge flue gas from said vessel.

21. The method of claim 1 where steam is employed to purge flue gas from said vessel and provide a steam blanket for said incandescent carbon.

* * * * *